(12) United States Patent
Goldstein

(10) Patent No.: US 7,057,194 B2
(45) Date of Patent: Jun. 6, 2006

(54) RADIATION BARRIER

(75) Inventor: James A. Goldstein, Bloomfield Hills, MI (US)

(73) Assignee: ECO Cath-Lab Systems, Inc., Bloomfield Hills, MI (US)

(*) Notice: Subject to any disclaimer, the term of this patent is extended or adjusted under 35 U.S.C. 154(b) by 101 days.

(21) Appl. No.: 10/819,739

(22) Filed: Apr. 7, 2004

(65) Prior Publication Data

US 2006/0076522 A1 Apr. 13, 2006

(51) Int. Cl.
*G21C 11/00* (2006.01)
*G21F 1/00* (2006.01)
*G02B 5/00* (2006.01)
*H01J 1/52* (2006.01)

(52) U.S. Cl. .................. 250/515.1; 250/505.1
(58) Field of Classification Search .............. 250/515.1
See application file for complete search history.

(56) References Cited

U.S. PATENT DOCUMENTS

| | | | |
|---|---|---|---|
| 1,907,523 A | 5/1933 | Egressi et al. | |
| 3,299,270 A | 1/1967 | D'Avella | |
| 3,308,297 A * | 3/1967 | Mansker | 250/515.1 |
| 3,904,695 A | 9/1975 | Hendrickx et al. | |
| 3,924,374 A | 12/1975 | Volper | |
| 4,062,518 A | 12/1977 | Stivender et al. | |
| 4,074,141 A | 2/1978 | Bryant | |
| 4,400,623 A | 8/1983 | Jacobson | |
| 4,460,833 A | 7/1984 | Malamud et al. | |
| 4,510,939 A | 4/1985 | Brenman et al. | |
| 4,514,640 A | 4/1985 | Bagnell et al. | |
| 4,581,538 A * | 4/1986 | Lenhart | 250/519.1 |
| 4,638,166 A | 1/1987 | Baudro | |
| 4,729,869 A | 3/1988 | Schukei et al. | |
| 4,905,265 A | 2/1990 | Cox et al. | |
| 4,938,233 A | 7/1990 | Orrison, Jr. | |
| 4,977,585 A | 12/1990 | Boyd et al. | |
| 4,982,744 A | 1/1991 | Stanec | |
| 5,006,718 A | 4/1991 | Lenhart | |
| 5,029,941 A | 7/1991 | Twisselmann | |
| 5,090,044 A | 2/1992 | Kobayashi | |
| 5,138,138 A | 8/1992 | Theilacker et al. | |
| 5,417,225 A | 5/1995 | Rubenstein et al. | |
| 5,442,729 A | 8/1995 | Kramer et al. | |
| 5,483,562 A | 1/1996 | Kornfeldt et al. | |
| 5,490,716 A | 2/1996 | Naughton | |
| 5,506,882 A | 4/1996 | O'Farrell, Jr. et al. | |
| 5,564,438 A | 10/1996 | Merchant | |

(Continued)

FOREIGN PATENT DOCUMENTS

DE 1128950 B 5/1962

OTHER PUBLICATIONS

Balter, "An Overview of Radiation Safety Regulatory Recommendations and Requirements," Catheterization and Cardiovascular Interventions, 1999, pp. 469-474, vol. 47.

(Continued)

*Primary Examiner*—John R. Lee
*Assistant Examiner*—Jennifer Yantorno
(74) *Attorney, Agent, or Firm*—Sonnenschein Nath & Rosenthal LLP

(57) ABSTRACT

A radiation barrier for shielding a person from radiation emitted from a radiation source. The barrier includes a radiopaque wall extending between opposite lateral edges, wherein the wall is positionable between the radiation source and the person to prevent radiation from traveling directly between the radiation source and the person, and a radiopaque deflector extending from the wall and obliquely angled relative to the wall.

67 Claims, 12 Drawing Sheets

U.S. PATENT DOCUMENTS

| | | | |
|---|---|---|---|
| 5,586,163 | A | 12/1996 | Goldstein |
| 5,613,254 | A | 3/1997 | Clayman et al. |
| 5,632,275 | A | 5/1997 | Browne et al. |
| 5,636,259 | A | 6/1997 | Khutoryansky et al. |
| 5,842,987 | A | 12/1998 | Sahadevan |
| 5,851,182 | A | 12/1998 | Sahadevan |
| 5,980,472 | A | 11/1999 | Seyl |
| 5,981,964 | A * | 11/1999 | McAuley et al. ........ 250/515.1 |
| 5,994,706 | A | 11/1999 | Allen et al. |
| 6,023,799 | A | 2/2000 | Wirth et al. |
| 6,104,779 | A | 8/2000 | Shepherd |
| 6,105,578 | A | 8/2000 | Sommers et al. |
| 6,224,548 | B1 | 5/2001 | Gopinathan et al. |
| 6,248,064 | B1 | 6/2001 | Gopinathan et al. |
| 6,282,264 | B1 | 8/2001 | Smith et al. |
| 6,325,538 | B1 | 12/2001 | Heesch |
| 6,334,852 | B1 | 1/2002 | Seyl |
| 6,448,571 | B1 | 9/2002 | Goldstein |
| 6,463,701 | B1 | 10/2002 | Baloga |
| 6,520,940 | B1 | 2/2003 | Gomez |
| 6,595,918 | B1 | 7/2003 | Gopinathan et al. |
| 6,653,648 | B1 | 11/2003 | Goldstein |
| 6,835,945 | B1 * | 12/2004 | Mossor et al. ........... 250/515.1 |

OTHER PUBLICATIONS

Clark, "Editorial Comment: How Much is Too Much?," Catheterization and Cardiovascular Interventions, 2000, p. 285, vol. 51.

Livingston, "Obesity and Its Surgical Management," Am. J. Surg., 2002, pp. 103-113, vol. 184.

Nuclear Associates, "Clear-Pb Lead-Plastic Multipurpose Adjustable-Height Mobile Barrier," 2000, 6 pages.

Podnos et al., "Complications After Laparoscopic Gastric Bypass," Arch. Surg., 2003, pp. 957-961, vol. 138.

Randall et al., "Neuro-Oncology Update: Radiation Safety and Nursing Care During Interstitial Brachytherapy," J. Neuroscience Nursing, 1987, pp. 315-320, vol. 19.

Ross et al., "Prevalence of Spinal Disc Disease Among Interventional Cardiologists," The American Journal of Cardiology, 1997, pp. 68-70, vol. 79.

Sewchand et al., "Radiation Control in the Intensive Care Unit for High Intensity Iridium-192 Brain Implants," Neurosurgery, 1987, pp. 584-588, vol. 20.

Stocker, "Management of the Bariatric Surgery Patient," Endocrinol. Metab. Clin. N. Am., 2003, pp. 437-457, vol. 32.

Worldwide Innovations & Technologies, Inc., Breakthrough Technology in Radiation Protection, 3 pages.

Innovative, Ergonomic, Protective Solutions, RayShield® by AADCO Medical, Inc. brochure.

* cited by examiner

FIG. 4
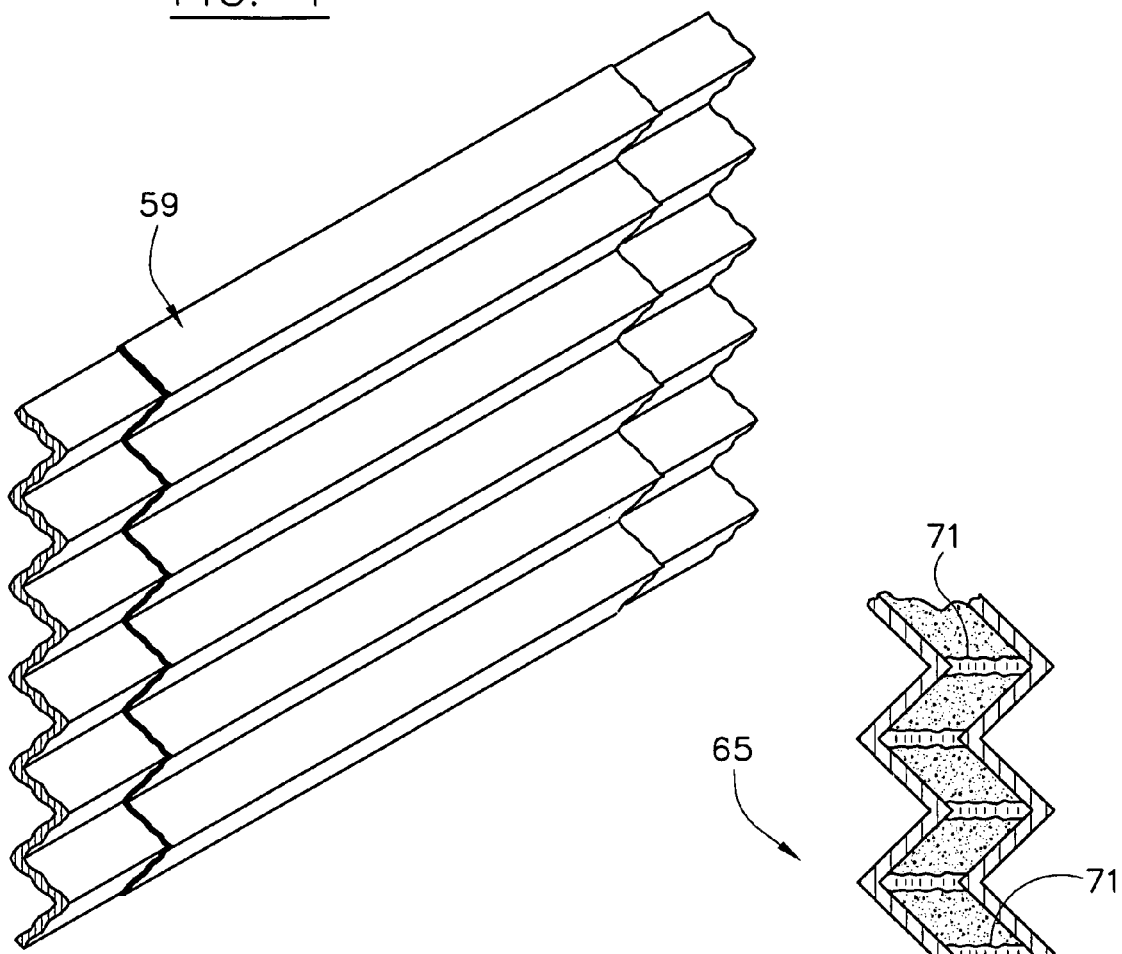
FIG. 5
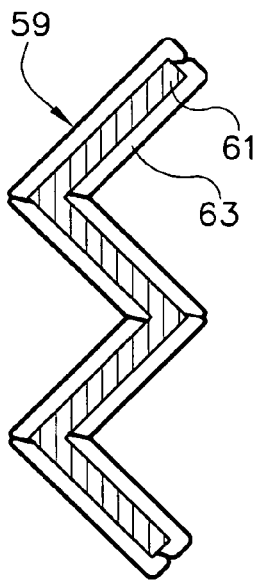
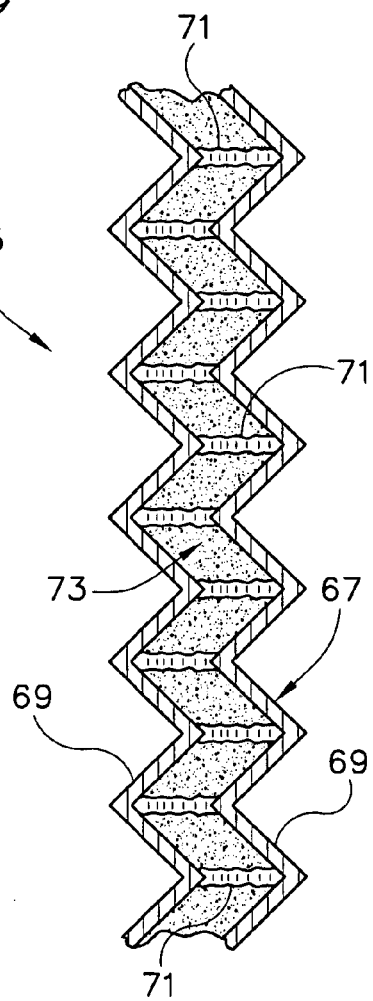
FIG. 6

FIG. 9
FIG. 10
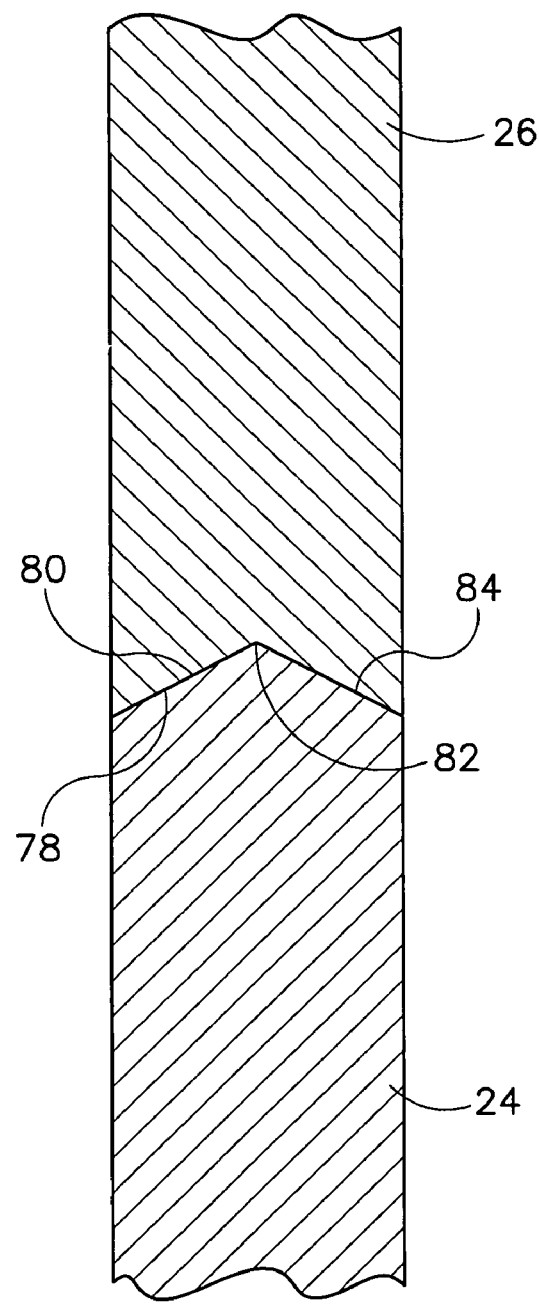
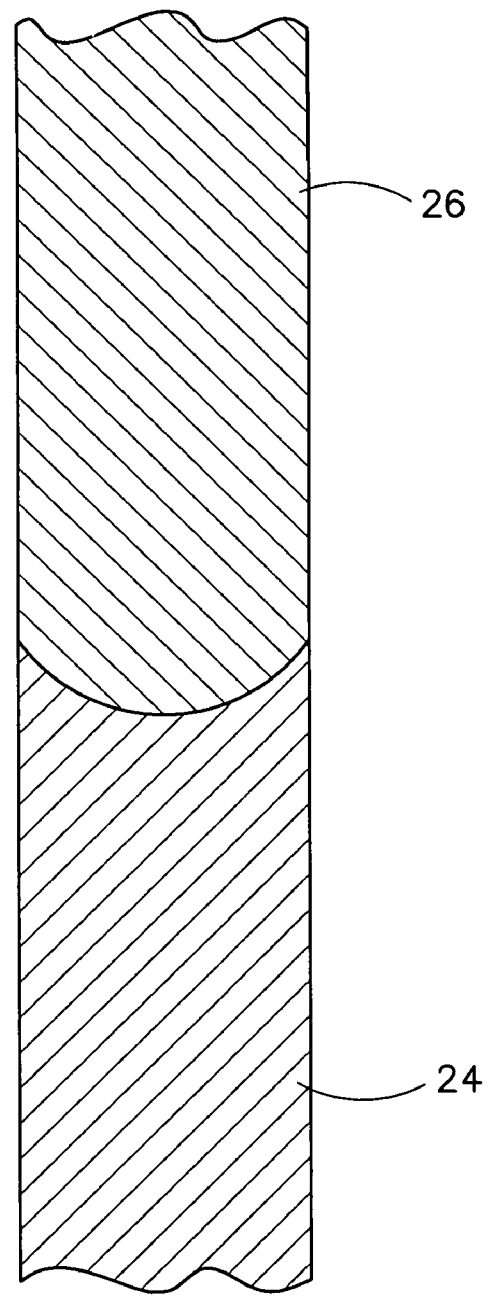

RADIATION BARRIER

BACKGROUND OF THE INVENTION

The present invention relates generally to radiation barriers, and more specifically to radiation barriers for shielding a person from radiation emitted during a medical procedure.

Radiation is emitted from equipment used in a wide variety of medical procedures. For example, radiation is emitted by radiographic or x-ray machines used by cardiologists when performing angioplasty procedures. Medical personnel are exposed to radiation during these procedures. Exposure to radiation over extended periods of time, even if the exposure is to low level radiation, may be toxic and cause a wide variety of health problems. Because patients undergo a limited number of exposures, cumulative radiation exposure is rarely a significant health concern to patients. However, medical personnel may perform many procedures per year over many years, and therefore may be exposed to significant cumulative radiation doses over time.

To reduce exposure, both fixed and moveable radiation shields may be used to minimize radiation exposure. Such shields are typically radiopaque plates (e.g., lead plates) positioned directly between the medical personnel and the radiation source(s). However, medical personnel may still be exposed to radiation reflected or scattered by objects, such as the table supporting the patient, the walls of the room, and even the patient. Medical personnel who must remain in the room usually wear radiation protection clothing, including full lead aprons, thyroid collars and leaded glasses, to further reduce exposure. However, the lead aprons, collars and glasses may not fully protect the personnel as substantial portions of legs, arms, and head remain exposed. Thus, despite the use of radiation protection clothing and shields, medical personnel may be exposed to amounts of radiation over time that harm the personnel. Additionally, the lead aprons and other radiation protection clothing is often very heavy, possibly leading to long term health problems such as disabling spinal injury.

SUMMARY OF THE INVENTION

In one aspect, the present invention includes a radiation barrier for shielding a person from radiation emitted from a radiation source. The barrier includes a radiopaque wall extending between opposite lateral edges. The wall is positionable between the radiation source and the person to prevent radiation from traveling directly between the radiation source and the person. The barrier also includes a radiopaque deflector extending from the wall and obliquely angled with respect to the wall.

In another aspect, the present invention includes a wall for shielding a person from radiation emitted from a radiation source. The wall includes a radiopaque lower section and a radiopaque upper section mountable on the lower section. The upper section has an opening sized and shaped for accommodating a portion of a table for supporting a patient and a portion of the patient supported by the table. The upper section and the lower section are positionable between the radiation source and the person to prevent radiation from traveling directly between the radiation source and the person.

In another aspect, the present invention includes a barrier for shielding a person from radiation emitted from a radiation source. The barrier includes a radiopaque central portion positionable between the radiation source and the person to prevent radiation from traveling directly between the radiation source and the person, and a radiopaque margin at least partially surrounding the central portion. The margin is obliquely angled with respect to the central portion.

In another aspect, the present invention includes a radiation barrier for shielding a person from radiation emitted from a radiation source. The barrier includes a radiopaque wall positionable between the radiation source and the person to prevent radiation from traveling directly between the radiation source and the person. The wall has an opening for accommodating a portion of the radiation source and a radiopaque cover positioned over the opening for preventing radiation emitted from the radiation source from passing through the opening to the person.

In yet another aspect, the present invention includes a radiation barrier for shielding a person from radiation emitted from a radiation source. The barrier includes a radiopaque wall extending between opposite lateral edges. The wall is positionable between the radiation source and the person to prevent radiation from traveling directly between the radiation source and the person. The barrier also includes a radiopaque deflector pivotally attached to the wall.

In still another aspect, the present invention includes a radiation barrier for shielding a person from radiation emitted from a radiation source. The barrier includes a radiopaque wall positionable between the radiation source and the person to prevent radiation from traveling directly between the radiation source and the person. The barrier also includes a plurality of radiopaque deflectors obliquely angled with respect to at least a portion of the wall.

Other features of the present invention will be in part apparent and in part pointed out hereinafter.

BRIEF DESCRIPTION OF THE DRAWINGS

FIG. 4 is a perspective of a portion of an accordion structure of a first embodiment;

FIG. 5 is a cross section of the structure shown in FIG. 4;

FIG. 6 is a cross section of an accordion structure of a second embodiment;

FIG. 9 is a fragmentary cross section of upper and lower sections of a wall of a barrier of a first embodiment;

FIG. 10 is a fragmentary cross section of upper and lower sections of a wall of a barrier of a second embodiment;

Corresponding reference characters indicate corresponding parts throughout the several views of the drawings.

DETAILED DESCRIPTION OF THE PREFERRED EMBODIMENT

Figure 1:
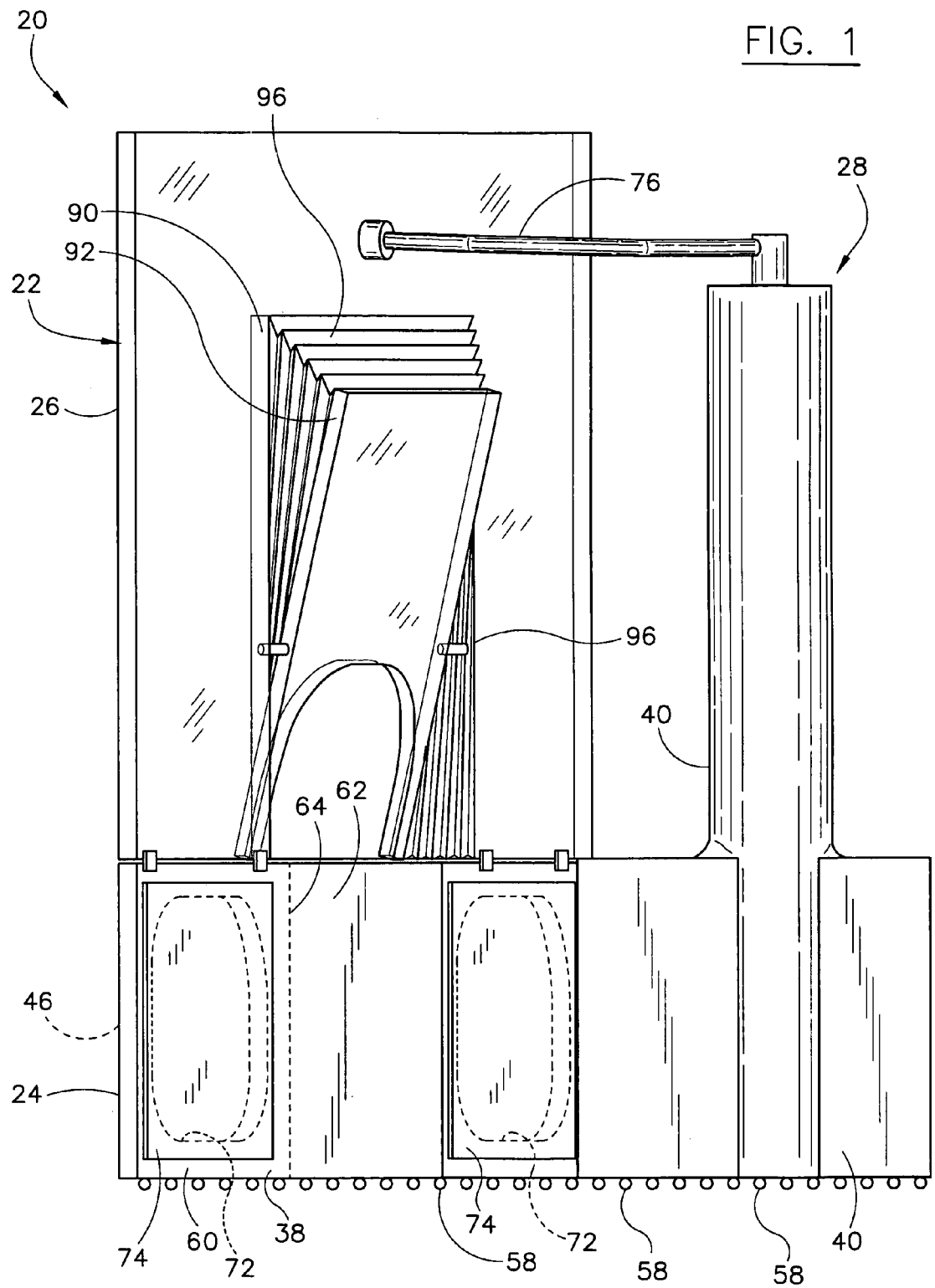
FIG. 1 is a perspective of a radiation barrier of the present invention.
Figure 2:
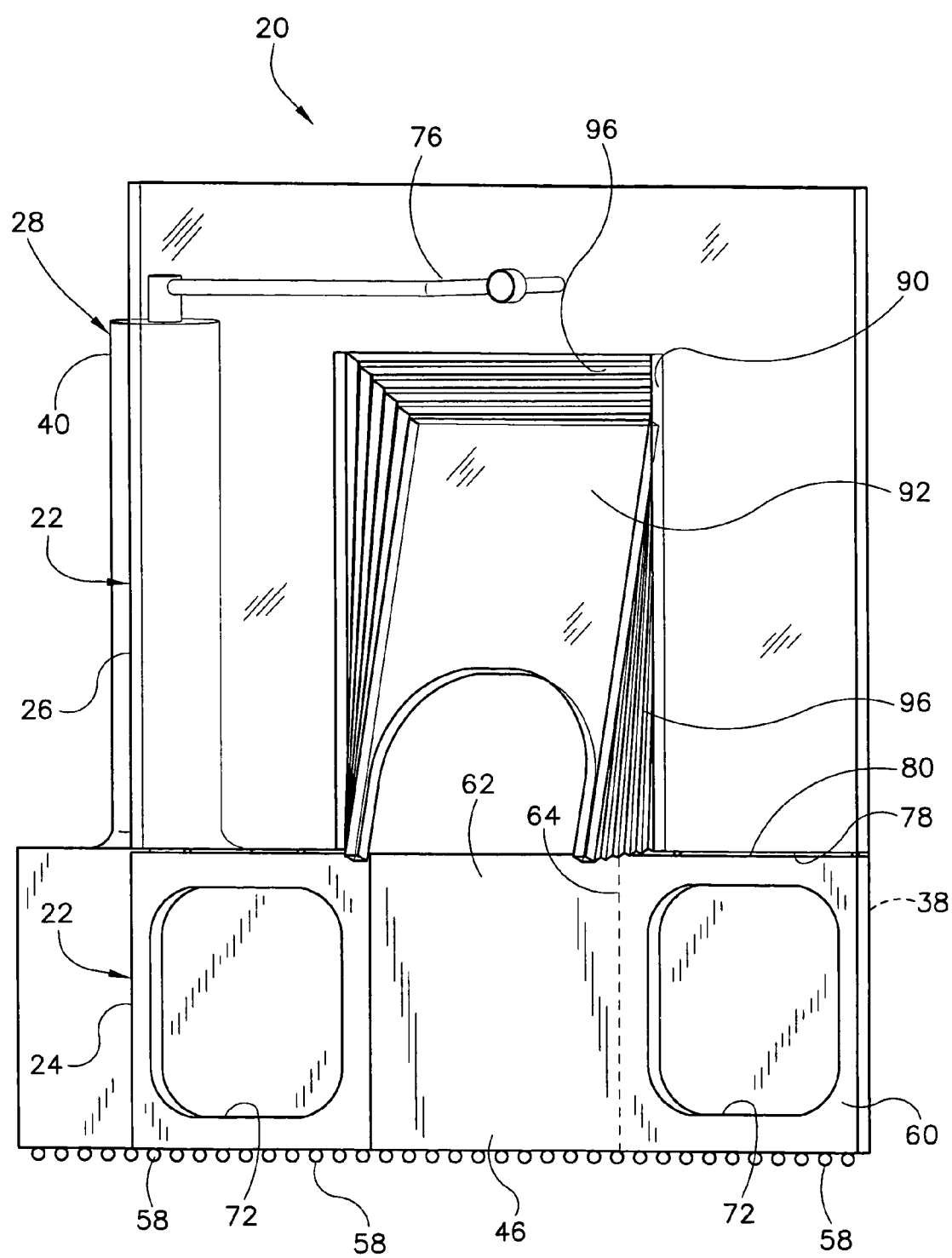
FIG. 2 is another perspective of the radiation barrier shown in FIG. 1.
Figure 3:
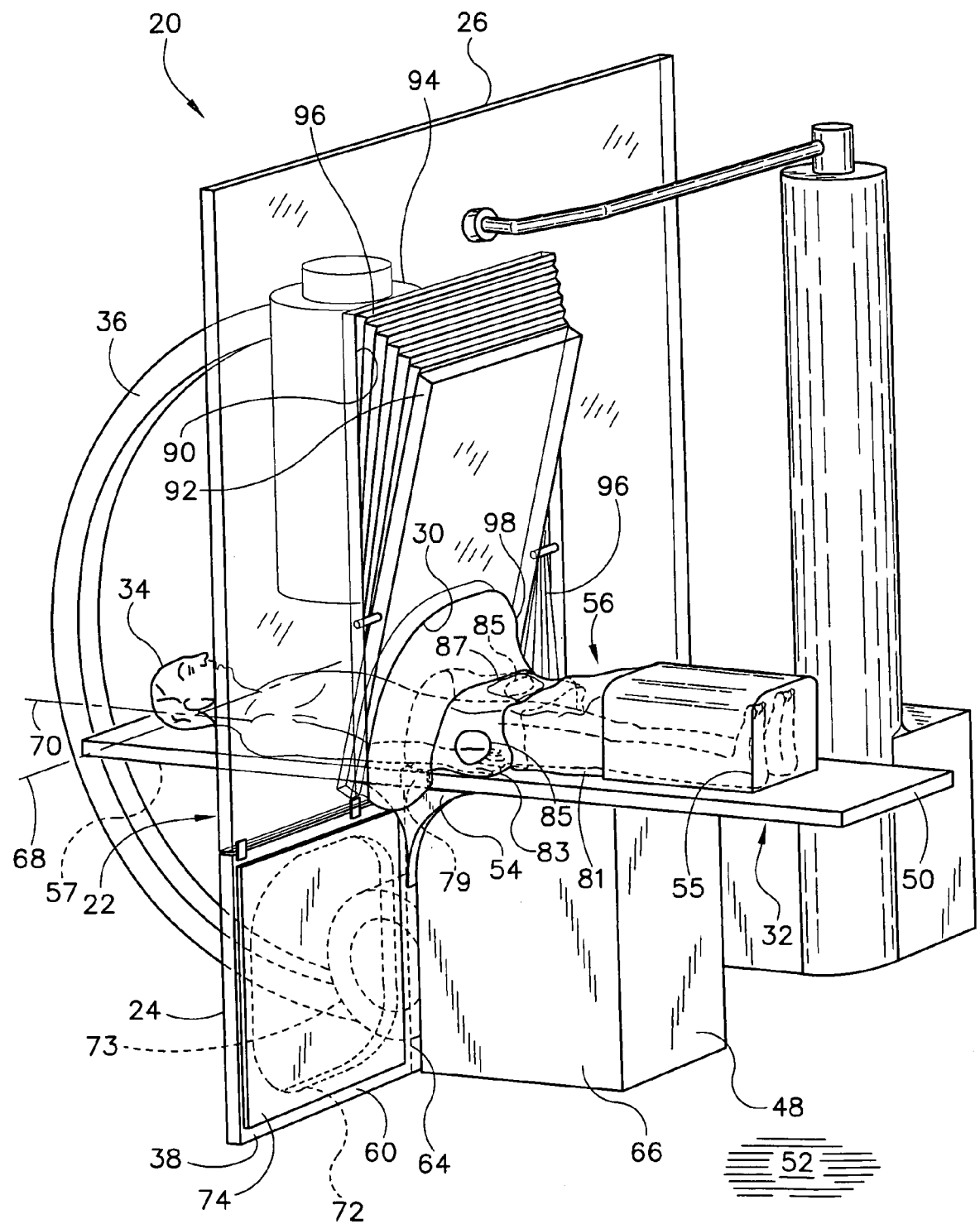
FIG. 3 is a perspective of the radiation barrier illustrated in FIGS. 1 and 2 in combination with a radiation source, a patient, and a table supporting the patient.

Referring now to the drawings, and more specifically to FIGS. 1 and 2, a radiation barrier of a first embodiment of the present invention is designated in its entirety by the reference numeral 20. The barrier 20 includes a radiopaque wall, generally designated by 22, having a radiopaque lower section 24 and a radiopaque upper section 26 detachably mountable on the lower section. As used herein, the term "radiopaque" is intended to mean generally opaque to various forms of radiation. Although other equivalencies may be used without departing from the scope of the present invention, in one embodiment "radiopaque" is intended to mean something having a lead equivalence of at least about 0.3 mm (i.e., capable of blocking as much radiation as a sheet of lead about 0.3 mm thick). A support, generally designated by 28, is attached to the upper section 26 and the lower section 24 for supporting the upper and lower sections. As illustrated in FIG. 3, the wall 22, and more specifically the upper section 26, includes an opening 30 for accommodating a portion of a table (generally designated by 32) and a portion of a patient 34 supported by the table. The wall 22 is positionable between a radiation source 36 (e.g., an x-ray source) and a person (e.g., medical personnel) to prevent radiation from traveling directly between the source and the person for shielding the person from radiation emitted from the source.

As illustrated in FIG. 1, the lower section 24 has a first side 38 that abuts a base 40 of the support 28. Other supports (not shown) may be attached to the wall 22 as desired to provide additional stability for the lower section 24 and/or the upper section 26 of the wall 22. Although other materials may be used without departing from the scope of the present invention, in one embodiment the lower section comprises a radiopaque material such as lead, lead plastic, leaded acrylic, leaded glass, lead rubber, and/or lead vinyl. As illustrated in FIG. 3, the lower section 24 is positionable between a base 48 of the table 32 and the radiation source 36, and between a top 50 of the table and a floor 52 supporting the table. When in position between the radiation source 36 and the person, the lower section 24 prevents some radiation emitted from the source 36 from traveling below the table top 50 to the person.

To facilitate a radiopaque seal between the lower section 24 and the table 32, a flexible radiopaque harness 54 may seal the lower section to the table as further illustrated in FIG. 3. In one embodiment, the harness 54 is attachable to the lower section 24 and the table 32 using suitable fasteners (e.g., zippers, buttons, magnets, adhesives, hooks, snap fasteners, or hook and loop fasteners). Alternatively, the harness 54 is attachable to the table 32 so it overlaps a portion of the lower section 24 and the table to seal the lower section to the table as shown in FIG. 3. In one embodiment, the harness 54 extends along a bottom surface 57 of the table top 50 and at least a portion thereof is positionable between the table base 48 and the lower section 24 of the wall 22 to further seal the lower section 24 to the table 32 as shown in FIG. 3. Specifically, in the illustrated embodiment the harness 54 has a generally triangular cross section to facilitate sealing the gap between the lower section 24 and the table 32, and to facilitate maintaining the radiopaque seal during and after movement of the lower section relative to the table and vice versa. The harness 54 may be attachable to the bottom surface 57 using suitable fasteners (e.g., zippers, buttons, magnets, adhesives, hooks, snap fasteners, or hook and loop fasteners). Alternatively, the harness 54 is attachable to the table top 50 using a strap 79 so the harness is held against the bottom surface 57 of the table top 50 as shown in FIG. 3. Although other materials may be used without departing from the scope of the present invention, in one embodiment the harness 54 comprises a radiopaque material such as lead, lead plastic, leaded acrylic, leaded glass, lead rubber, and/or lead vinyl.

The harness 54 may also be attachable (e.g., using zippers, buttons, magnets, adhesives, hooks, snap fasteners, or hook and loop fasteners) to a radiopaque drape (generally designated by 56) covering the legs, groin, and hips of the patient 34 to further seal the lower section 24 to the table 32 and prevent radiation from traveling from the patient to the person. The drape 56 is described in U.S. Pat. Nos. 6,448,571 and 6,653,648, both of which are incorporated by reference herein in their respective entireties. As shown in the embodiment of FIG. 3, the drape 56 includes a rigid radiopaque base 55, a flexible radiopaque middle blanket 81, and a flexible radiopaque access blanket 83. The base 55, the middle blanket 81, and the access blanket 83 overlap one another to provide a radiopaque seal. Additionally, the base 55, the middle blanket 81, and the access blanket 83 may be attachable to one another, using suitable fasteners (e.g., zippers, buttons, magnets, adhesives, hooks, snap fasteners, or hook and loop fasteners). The access blanket 83 may include at least one opening 85 to provide medical personnel access to the patient 34 (e.g., to monitor physiological parameters of the patient). The opening 85 may be covered with a radiopaque flap 87 when not in use to prevent radiation from traveling through the opening 85 to the person. Additionally, suitable radiopaque structures (not shown) may be used to seal the opening with equipment (not shown) and/or portions (not shown) of medical personnel extending through the opening 85 to prevent radiation from traveling through the opening. Although other materials may be used without departing from the scope of the present invention, in one embodiment the base 55, the middle blanket 81, and the access blanket 83 of the drape 56 each comprise a radiopaque material such as lead, lead plastic, leaded acrylic, leaded glass, lead rubber, and/or lead vinyl.

Figure 7:
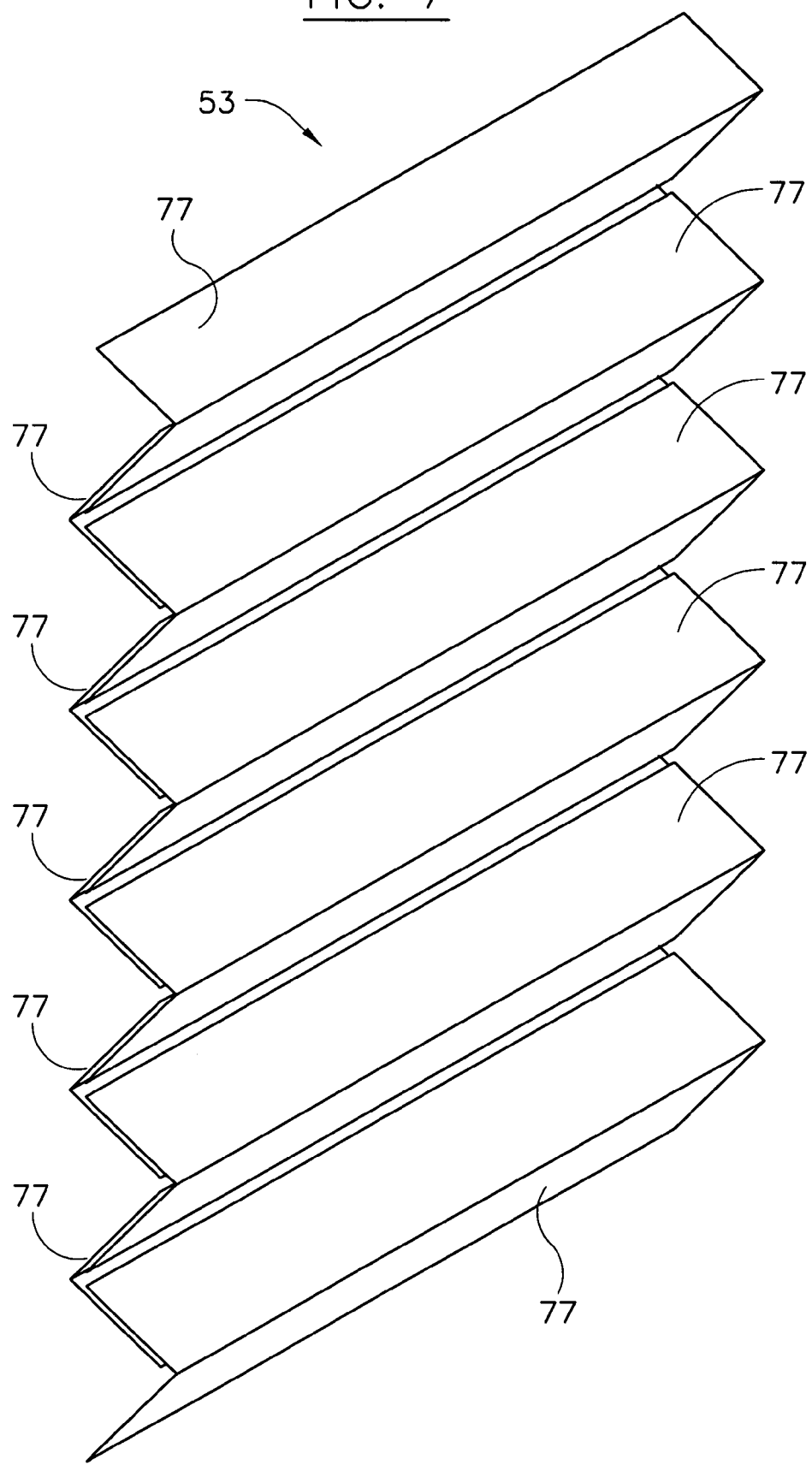
FIG. 7 is a perspective of an accordion structure of a third embodiment.

The flexible nature of the harness 54 (in addition to the shape of the embodiment of the harness shown in FIG. 3) allows free movement between the table 32 and the lower section 24 to facilitate positioning of the wall 22 and the patient 34 while still maintaining a radiopaque seal. In one embodiment, the harness 54 comprises an accordion structure (generally designated by 59) as shown in FIG. 4. Specifically, the structure 59 includes a frame 61 and a plurality of radiopaque and overlapping layers 63 covering the frame, as shown in FIG. 5. Alternatively, the harness 54 (FIG. 3) may comprise another accordion structure (generally designated by 65) as shown in FIG. 6. Specifically, the accordion structure 65 includes a frame (generally designated by 67) having two layers 69 spaced apart and connected together by a plurality of elastic members 71. The space between the layers 69 may be filled with radiopaque media (generally designated by 73) such as radiopaque microbeads, foam, gauze, or gel. Additionally, any surface of the layers 69 may be covered with a radiopaque material (not shown). In yet another embodiment, the harness 54 (FIG. 3)

may comprise yet another accordion structure (generally designated by 53) as shown in FIG. 7. The structure 53 includes a plurality of overlapping and interlocking radiopaque sheets 77.

To facilitate movement of the lower section 24 and positioning of the wall 22, the lower section may be supported by at least one caster 58 (e.g., a wheel, a roller, or ball bearing) as illustrated in FIGS. 1 and 2. Additionally, the support 28 may be supported by at least one caster 58 to further facilitate movement of the wall 22. The casters 58 may be provided with a locking mechanism (not shown) to allow selective movement of the wall 22 for positioning, and prevent movement of the wall when in position.

Figure 8:
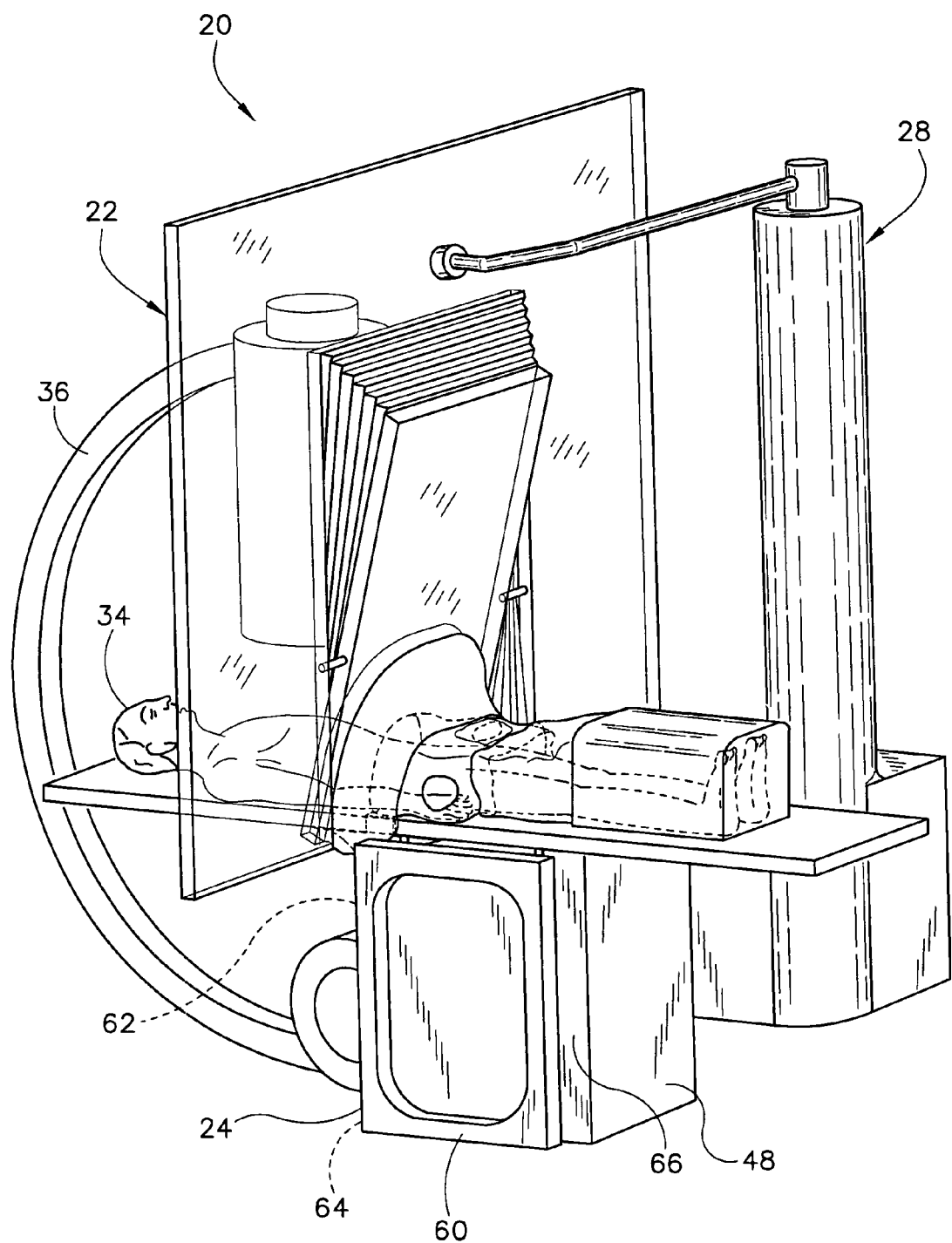
FIG. 8 is a perspective of the radiation barrier of the present invention illustrating a portion of the barrier folded back.

As illustrated in FIGS. 1–3 and 8, a portion of the lower section 24 may be moveable relative to the support 28 and the remainder of the lower section 24 to allow unobstructed access to the radiation source 36 (FIGS. 3 and 8) and a portion of the patient adjacent the source when the wall 22 is positioned between the source and the person. More specifically, in one embodiment a portion 60 of the lower section 24 is pivotally attached to a remainder 62 of the lower section with a hinge 64 to allow the portion to be folded out of the way (e.g., folded back at least partially against a surface 66 (FIGS. 3 and 8) of the table base 48 as shown in FIG. 8). Alternatively, the lower section 24 may include a plurality of panels (not shown) slidably attached to one another such that the panels can be selectively telescoped outward from the support 28 to position the lower section 24 between the radiation source 36 and the person, and retracted toward the support to allow unobstructed access to the source and the patient 34 (FIGS. 3 and 8).

As illustrated in FIG. 3, the radiation source 36 may be rotated about a lateral axis 68 and/or about a longitudinal axis 70 to position the source so radiation is directed along a particular line through the patient 34. The lower section 24 includes at least one opening 72 (also shown in FIGS. 1 and 2) for accommodating a portion (e.g., the portion 73 shown in FIG. 3) of the radiation source 36. A flexible radiopaque panel 74 (also shown in FIG. 1) may be positioned over the opening 72 to allow the opening to accommodate a portion of the radiation source 36 while preventing radiation emitted from the source from passing through the opening to the person. Although other materials may be used without departing from the scope of the present invention, in one embodiment the panel 74 comprises a radiopaque material such as lead, lead plastic, leaded acrylic, leaded glass, lead rubber, and/or lead vinyl. Additionally, although the panel 74 may be formed from other structures without departing from the scope of the present invention, in one embodiment the panel is formed from at least one of the accordion structure 59 shown in FIG. 4, the accordion structure 65 shown in FIG. 6, and the accordion structure 53 shown in FIG. 7. Alternatively, the panel 74 may be a panel (or other suitable arrangement) rotatably attached to the lower section 24 adjacent the opening 72 as will be described below with respect to the upper section 26.

In one embodiment, the lower section 24 includes at least a portion that, in addition to being radiopaque as discussed above, is transparent to visible light to allow the person to view the radiation source 36 and/or the portion of the patient 34 adjacent the source when the wall 22 is positioned between the source and the person.

As illustrated in FIGS. 1 and 2, the support 28 includes a movable and articulated arm 76 for supporting the upper section 26. More specifically, the movable arm 76 is attached to the base 40 of the support 28 and is movable relative to the support for selectively attaching and detaching the upper section 26 to and from the lower section 24. The arm 76 is sufficiently rigid that it supports the upper section 26 when detached from the lower section 24. To position the wall 22 between the radiation source 36 (FIG. 3) and the person (FIG. 3), the lower section 24 may be positioned as described above while the upper section 26 is separated from it. The upper section 26 may then be moved relative to the lower section 24 and lowered onto the lower section such that the upper section is positioned between the radiation source 36 and the person and such that portions of the table 32 and the patient 34 are positioned in the opening 30. The upper and lower, 26, 24, respectively, sections are separable to facilitate positioning patients on the table 32. Further, it is envisioned that separating the barrier 20 may take up less space during storage or transport.

The upper section 26 may be attached to the lower section 24 using any suitable means (e.g., hook and loop fasteners, snap fasteners, or bolts and nuts). In one embodiment, a lower surface of the upper section 26 and an upper surface of the lower section 24 are adapted to interdigitate. For example, in one embodiment the lower surface 78 of the upper section 26 has a recess 82 for receiving a protrusion 84 of the upper surface 80 of the lower section 24 as shown in FIG. 9. An alternative rounded configuration shown in FIG. 10 is similar to the configuration shown in FIG. 9. This recess-and-protrusion arrangement at the joint between the upper and lower sections 26, 24 may make it easier to align the upper and lower sections, and may facilitate a more secure attachment between the upper and lower sections.

As described above and illustrated in FIG. 3, the radiation source 36 may be rotated about axes 68, 70. The upper section 26 includes an opening 90 for accommodating a portion (e.g., the portion 94 shown in FIG. 3) of the radiation source 36. Any of the openings 30, 72, 90 may be referred to herein as a first or a second opening. A radiopaque cover 92 is positioned over the opening 90 for preventing radiation emitted by the radiation source 36 from passing through the opening to the person. As shown in FIGS. 1–3, the cover 92 is pivotally attached to the upper section 26 adjacent the opening 90. Alternatively, the cover 92 may be a flexible radiopaque panel (or other suitable arrangement) positioned over the opening 90, similar to the radiopaque panel 74 described above, to allow the opening to accommodate a portion of the radiation source 36 (FIG. 3) while preventing radiation emitted from the source from passing through the opening. Although other materials may be used without departing from the scope of the present invention, in one embodiment the rotatable cover 92 comprises a radiopaque material such as lead, lead plastic, leaded acrylic, leaded glass, lead rubber, and/or lead vinyl.

Figure 11:
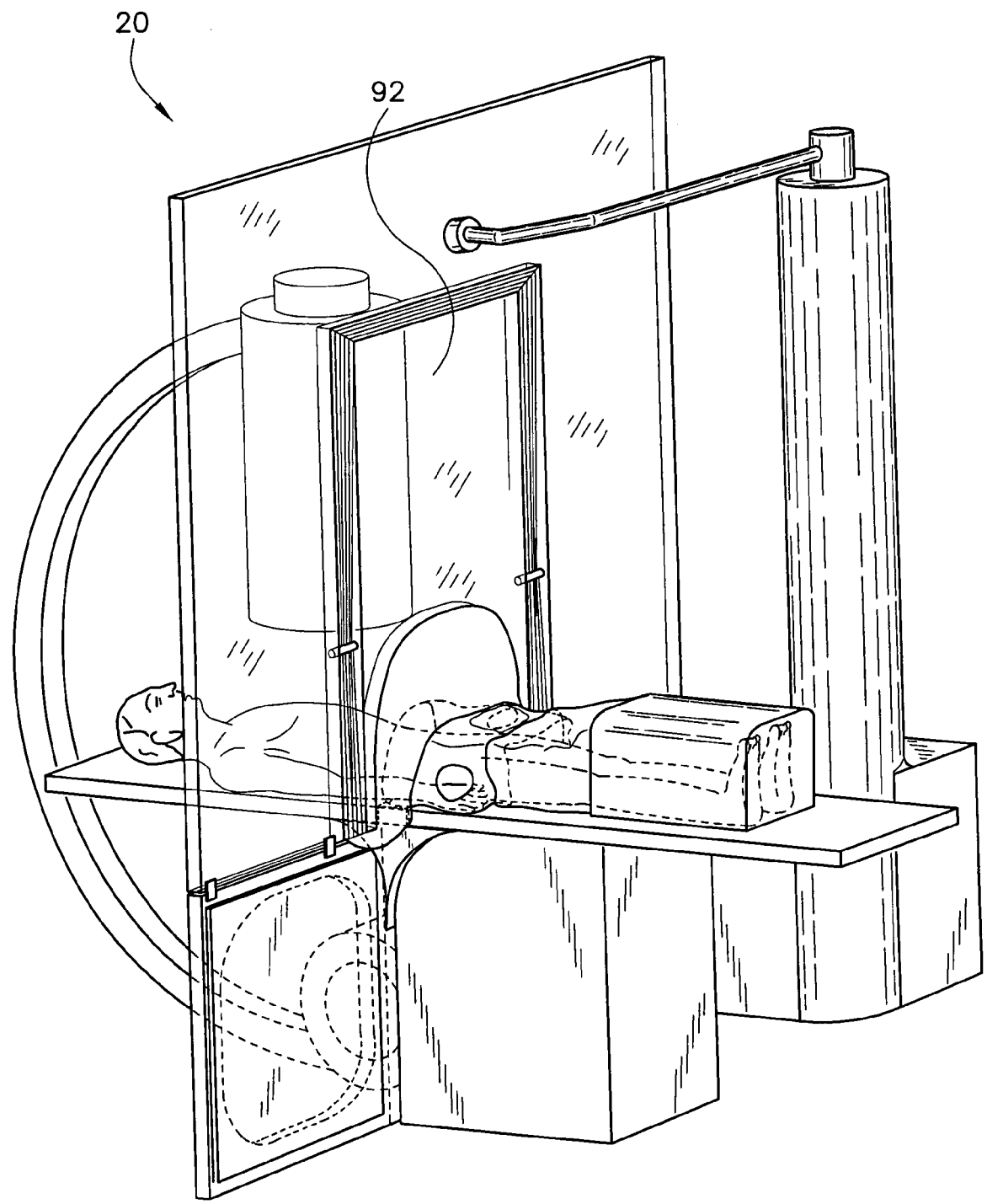
FIG. 11 is a perspective of the radiation barrier of the present invention illustrating a cover in a closed position.

The rotatable cover 92 has a closed position (FIG. 11) wherein at least a portion of the cover is generally parallel to the upper section 26 to block radiation emitted from the radiation source 36 from passing through at least a portion of the opening 90. The cover 92 also has an open position (FIGS. 1–3) in which the cover is angled with respect to the upper section 26 to allow a portion of the radiation source 36 (e.g., the portion 94 shown in FIG. 3) to be accommodated by the opening 90. The cover 92 moves from the closed position to the open position when engaged by the radiation source. In one embodiment, the cover 92 is biased to the closed position using any suitable biasing mechanism (e.g., springs, weights or magnets). A flexible radiopaque seal 96 spans between the cover 92 and the upper section 26 of the wall 22 to prevent radiation from passing between the cover and the upper section 26. Although other materials may be used without departing from the scope of the present invention, in one embodiment the seal 96 comprises a radiopaque material such as lead, lead plastic, leaded acrylic, leaded glass, lead rubber, and/or lead vinyl. Additionally, although the seal 96 may be formed from other structures without departing from the scope of the present invention, in one embodiment the seal is formed from at least one of the accordion structure 59 shown in FIG. 4, the accordion structure 65 shown in FIG. 6, and the accordion structure 53 shown in FIG. 7.

As described above, the upper section 26 has the opening 30 for accommodating a portion of the table 32 and a portion of the patient 34 supported by the table. In the illustrated embodiment, the opening is positioned along a lower edge of the cover 92. However, the opening 30 may be formed in any portion of the upper section 26 and the opening 30 may not be positioned in the cover 92. As illustrated in FIG. 3, a radiopaque skirt 98 is attachable to the upper section 26 (specifically the cover 92 in the embodiment shown in FIG. 3) adjacent the opening 30 for blocking radiation from passing through a space formed between the upper section and the patient 34 and/or the table 32. The skirt 98 may overlap a portion of the lower section 24 as shown in FIG. 3 to facilitate sealing the upper section 26 to the lower section 24. The skirt 98 may also be attachable to the drape 56 and/or the harness 54 (e.g., using zippers, buttons, magnets, adhesive, hooks, snap fasteners, or hook and loop fasteners) to further seal the upper section 26 to the patient and/or the table 32 and prevent radiation from traveling from the patient to the person. Although other materials may be used without departing from the scope of the present invention, in one embodiment the skirt 98 comprises a radiopaque material such as lead, lead plastic, leaded acrylic, leaded glass, lead rubber, and/or lead vinyl. Additionally, although the skirt 98 may be formed from other structures without departing from the scope of the present invention, in one embodiment the skirt is formed from at least one of the accordion structure 59 shown in FIG. 4, the accordion structure 65 shown in FIG. 6, and the accordion structure 53 shown in FIG. 7.

When the upper section 26 is attached to the lower section 24 and the wall 22 is positioned between the radiation source 36 and the person as shown in FIG. 3, the upper section prevents radiation from traveling over the lower portion 24 and/or the table top 50 to the person. As described above, the lower section 24 prevents radiation from traveling under the table top to the person.

In one embodiment, the upper section 26 includes at least a portion that, in addition to being radiopaque as discussed above, is transparent to visible light to allow the person to view the radiation source 36 and/or the portion of the patient 34 adjacent the source when the wall 22 is positioned between the source and the person. Additionally, similar to the lower portion described above, a portion (not shown) of the upper section 26 may be moveable relative to the support 28, the base 48 of the table 32, and the remainder of the upper section 26 to allow unobstructed access to the radiation source 36 and a portion of the patient 34 adjacent the source when the wall 22 is positioned between the source and the person.

Figure 12:
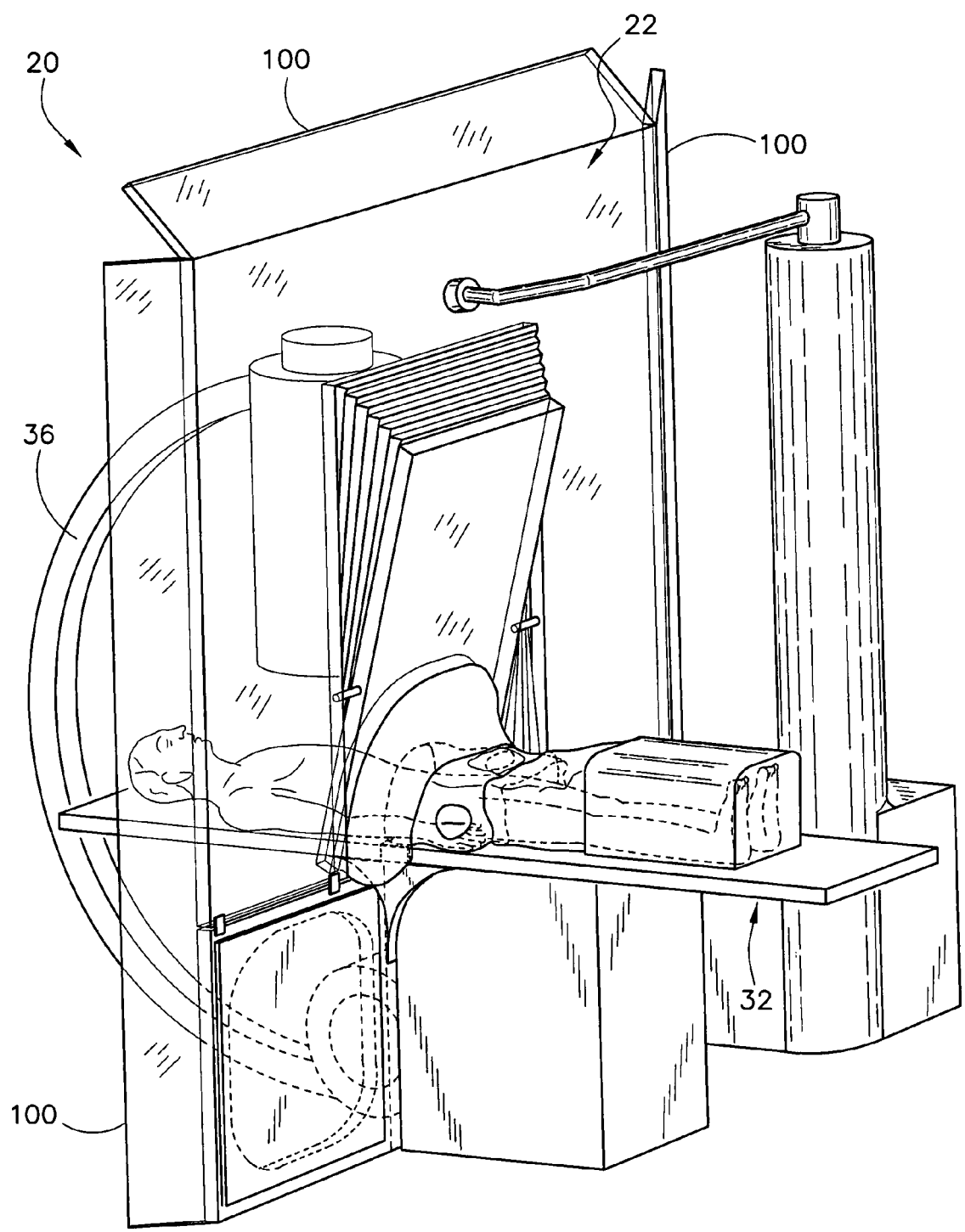
FIG. 12 is a perspective of one embodiment of the radiation barrier of the present invention including a plurality of deflectors.

As illustrated in FIG. 12, in one embodiment a plurality of radiopaque deflectors 100 extend from the wall 22. The deflectors 100 are each obliquely aligned with respect to the wall 22 to deflect radiation emitted from the radiation source 36 and thereby facilitate preventing radiation from traveling around the wall to the person. The deflectors 100 may be integrally formed with the wall 22 or alternatively may be separate components attached to the wall in any suitable manner. Although the barrier 20 is described and illustrated herein as having a plurality of deflectors 100, it should be understood that the barrier may have any number of deflectors (including no deflectors or only one deflector) without departing from the scope of the present invention. Additionally, although other materials may be used without departing from the scope of the present invention, in one embodiment the deflectors 100 comprise a radiopaque material such as lead, lead plastic, leaded acrylic, leaded glass, lead rubber, and/or lead vinyl.

Figure 13:
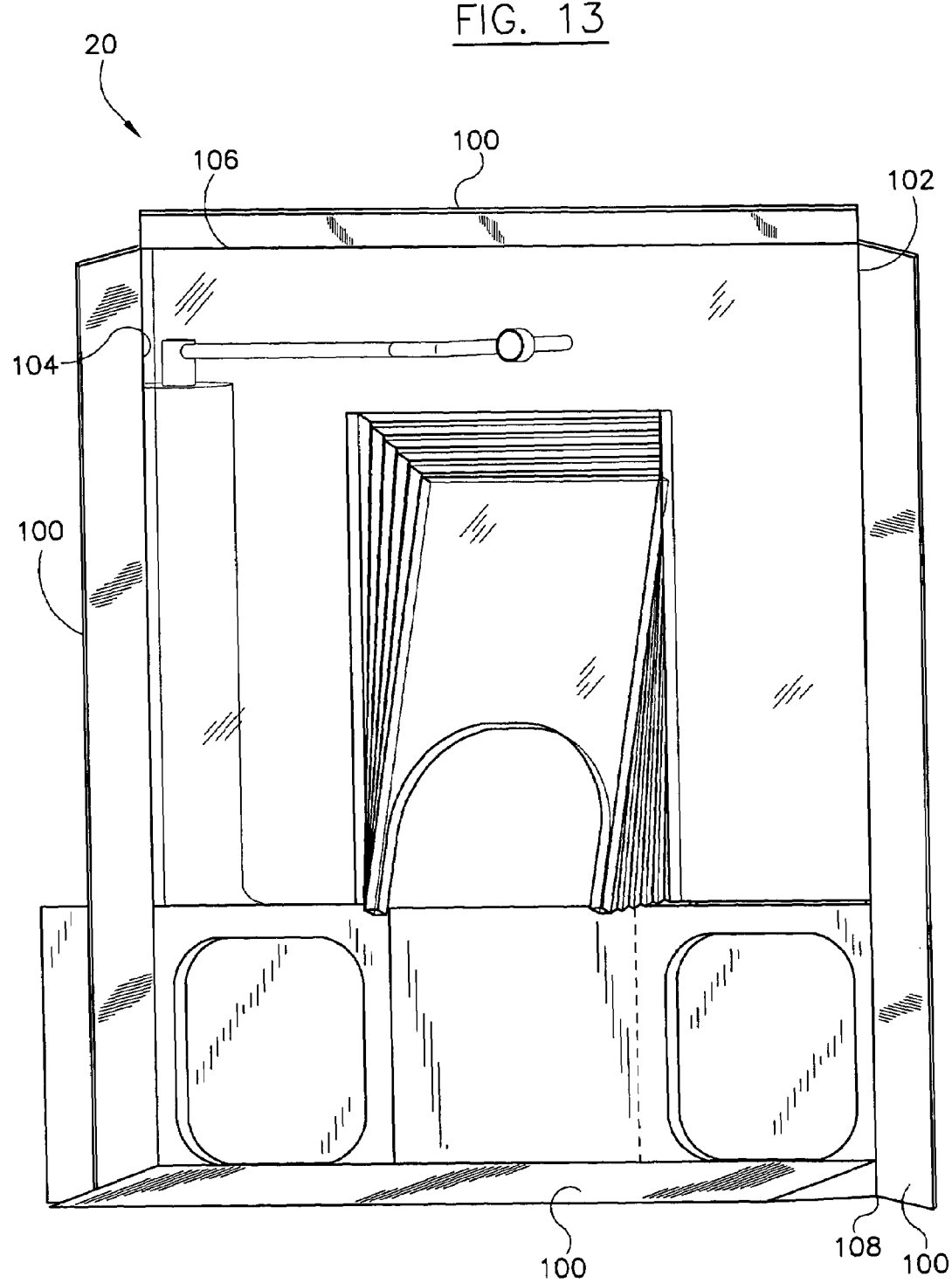
FIG. 13 is a perspective of another embodiment of the radiation barrier of the present invention.

The particular shape, number, configuration, and/or angle of each of the deflectors 100 with respect to the wall 22 may depend upon the configuration of the barrier 20, the radiation source 36, the table 32, the room (not shown) containing the radiation source, as well as any equipment or other items in the room. The deflectors 100 may be formed in any number, angle, and/or any configuration (including extending from anywhere on the wall 22) suitable to achieve the least possible radiation exposure to the person. For example, as illustrated in FIG. 13, the wall 22 extends between opposite lateral edges 102, 104, and also extends vertically between an upper edge 106 and a lower edge 108. In the embodiment illustrated in FIG. 13, each of the edges 102, 104, 106, 108 has a deflector 100 extending therefrom. The deflectors 100 extending from the respective lateral edges 102, 104 deflect radiation emitted from the radiation source 36 (FIGS. 3, 8, and 12) to facilitate preventing radiation from traveling around the lateral edges 102, 104 of the wall 22. Similarly, the deflector 100 extending from the upper edge 106 facilitates preventing radiation from traveling around (over) the upper edge 106, and the deflector 100 that extends from the lower edge 108 facilitates preventing radiation from traveling around (under) the lower edge 108. When the barrier 20 includes the deflectors 100 extending from edges of the wall 22 as shown in FIG. 13, the wall 22 forms a radiopaque central portion of the barrier 20 and the deflectors 100 form radiopaque margins that at least partially surround the wall and are obliquely aligned with respect to the wall. In the illustrated embodiment, the wall 22 is generally planar and rectangular. However, it should be understood that the wall 22 may have any suitable shape and may be shaped other than planar and rectangular without departing from the scope of the present invention. Similarly, the deflectors 100 may have any suitable shape including shapes other than planar and rectangular.

Figure 14:
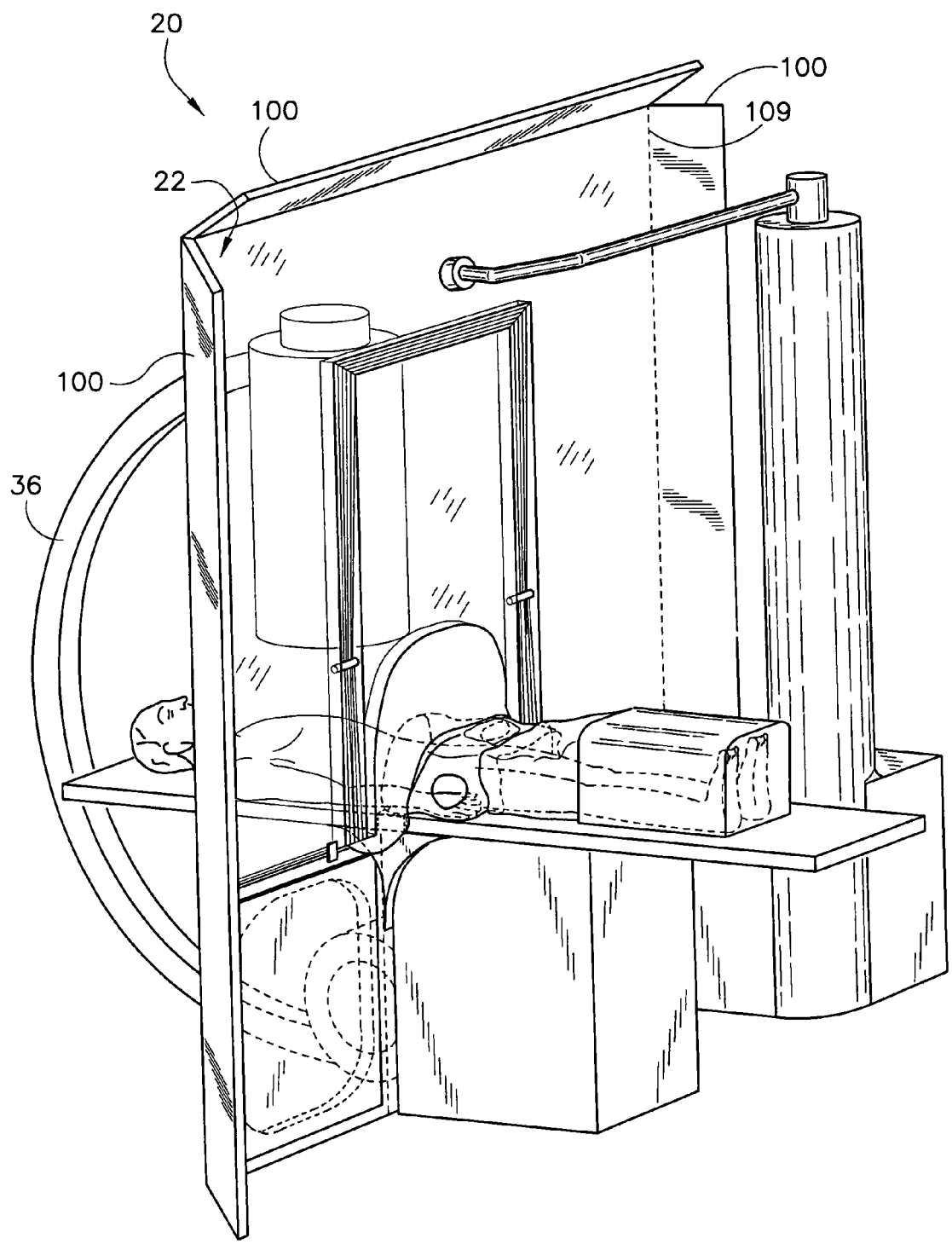
FIG. 14 is a perspective of yet another embodiment of the radiation barrier of the present invention.

In the embodiments illustrated in FIGS. 12 and 13, the deflectors 100 each extend generally toward the radiation source 36. However, in some circumstances the person (FIGS. 12 and 14) may be exposed to the least amount of radiation when the deflectors 100 extend generally away from the radiation source 36, as shown in FIG. 14. The angle of the deflectors 100 with respect to the wall 22 may be particularly important to reducing the person's exposure. Although other angles may be used without departing from the scope of the present invention, in one embodiment the deflectors 100 are angled between about 100 and about 170 degrees with respect to the wall 22. In one embodiment, the deflectors 100 are angled between about 140 and about 160 degrees with respect to the wall 22. In yet another embodiment, the deflectors 100 are angled about 150 degrees with respect to the wall 22. Additionally, as shown in FIG. 14 at least one of the deflectors 100 may be pivotally attached to the wall (e.g., using a hinge 109) so the angle of the deflectors with respect to the wall 22 can be selectively adjusted to achieve the least exposure.

Figure 15:
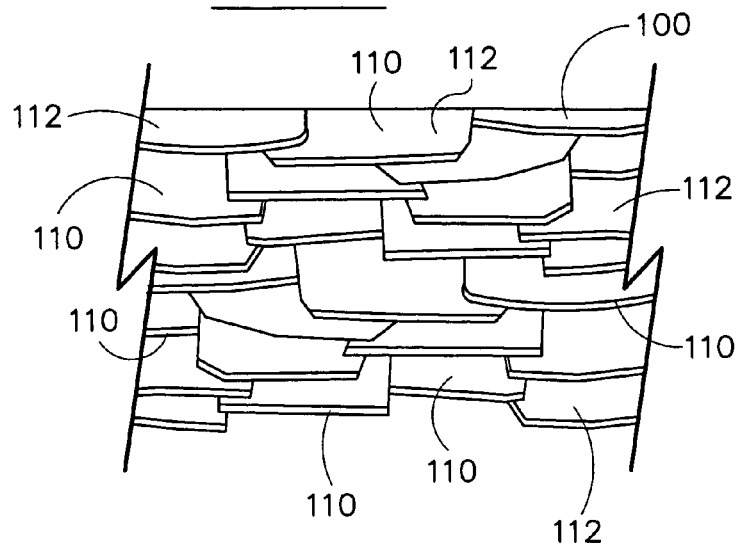
FIG. 15 is front elevation of a portion of a deflector of the present invention.
Figure 16:
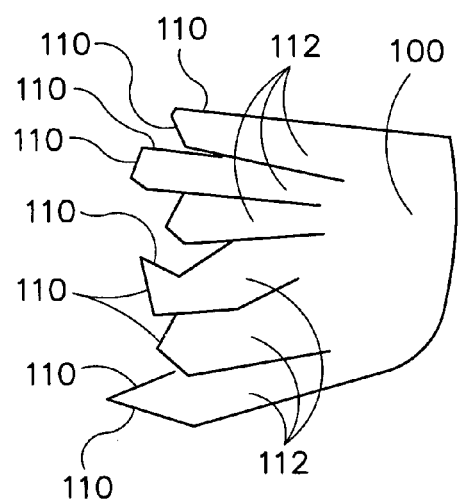
FIG. 16 is a side elevation of the deflector illustrated in FIG. 15.
Figure 17:
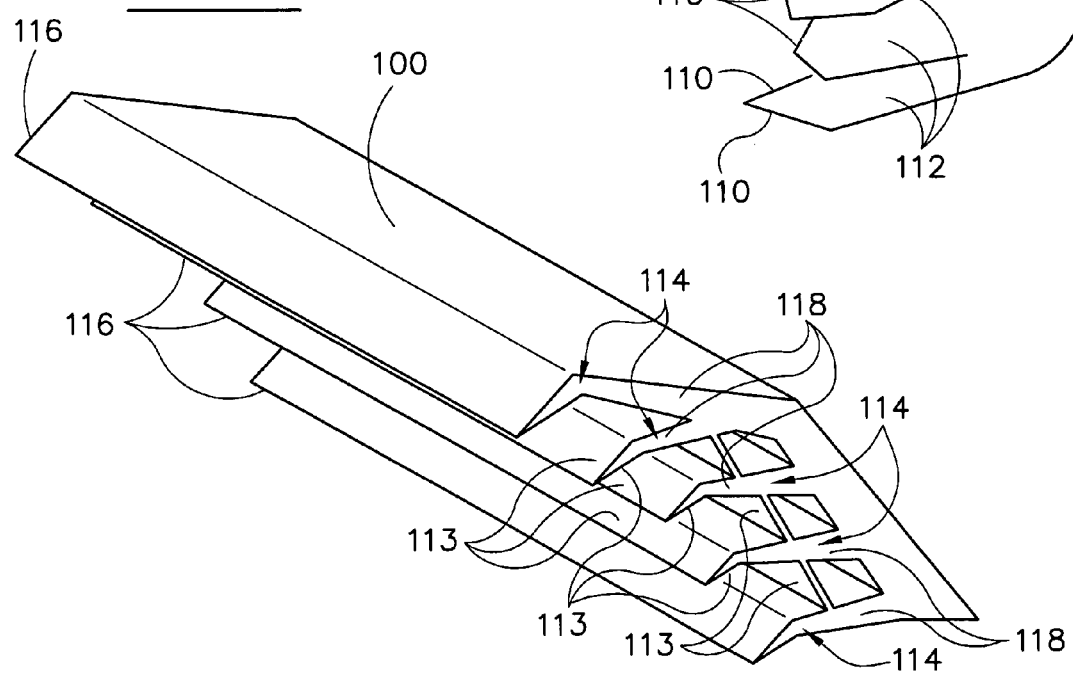
FIG. 17 is a perspective of another deflector of the present invention.

As illustrated in FIGS. 15–17, in one embodiment the deflectors 100 each have a plurality of surfaces (designated by 110 in FIGS. 15 and 16, and designated by 113 in FIG. 17). Each surface is obliquely angled with respect to at least some of the other surfaces of the respective deflector and/or with respect to at least some of the other surfaces of other deflectors. The shapes of the surfaces and angles of the surfaces relative to one another may baffle radiation emitted from the source 36 (FIGS. 3, 8, and 12) by absorbing the radiation and/or deflecting the radiation from one surface to another in a series of angles that causes the radiation to attenuate or dissipate as much energy as possible. For example, FIGS. 15 and 16 illustrate a deflector having a plurality of plates 112 arranged in overlapping layers to form surfaces 110. The plates 112 are alternately angled to catch and deflect radiation to adjacent plates on the respective deflector and/or other deflectors. The surfaces 110 may be macroscopic surfaces as shown in FIGS. 15 and 16, or alternatively may be microscopic surfaces. FIG. 17 illustrates another example wherein surfaces 113 baffle radiation emitted from the source 36 (FIGS. 3, 8, and 12) by absorbing and/or deflecting the radiation from one surface 113 to another. Specifically, the surfaces 113 are formed on a plurality of fingers (generally designated by 114) extending from the wall deflector 100. In the embodiment shown in FIG. 17, each of the plurality of fingers 114 includes a tip 116 obliquely angled relative to a base 118 of the respective finger. In one embodiment, some or all of the surfaces 113 include macroscopic and/or microscopic surfaces similar to the surfaces 110 shown in FIGS. 15 and 16.

In one embodiment the surfaces 110, 113 are formed from a material designed to absorb and/or deflect radiation to further baffle the radiation emitted from the source 36. As shown in FIG. 12, in one embodiment at least one of the deflectors 100 includes at least a portion that, in addition to being radiopaque as discussed above, is transparent to visible light to allow the person to view the radiation source 36 and/or the portion of the patient 34 adjacent the source when the wall 22 is positioned between the source and the person.

The above-described radiation barriers are cost-effective and reliable for shielding medical personnel from radiation emitted from a radiation source. Specifically, the barriers include a radiopaque wall that may be easily positioned between a radiation source and the personnel to shield the personnel from radiation emitted from the source. The wall includes an upper section and lower section to facilitate easy positioning of the barriers between the radiation source and the person, as well as convenient transport and storage of the barrier. The radiopaque wall may also include an opening to accommodate a portion of the radiation source so the wall does not interfere with operation of the source. The opening is sealed to prevent radiation from passing therethrough and therefore reduce the exposure to radiation emitted from the source. The barrier may also include at least one deflector extending from the wall and obliquely angled with respect to the wall to deflect radiation to prevent radiation from being reflected around the wall to the person. The deflectors may include obliquely aligned surfaces configured to baffle the radiation emitted by the source by absorbing the radiation and/or deflecting the radiation from one surface to another in a series of angles that causes the radiation to dissipate as much energy as possible. The barriers of the present invention are anticipated to reduce exposure to less than about 1% of the radiation emitted by the source. Accordingly, medical personnel may not be exposed to significant cumulative doses of radiation despite performing many procedures. Additionally, because the radiation barriers of the present invention may reduce exposure to non-threatening levels, medical personnel may not need to wear cumbersome and possibly injury-causing leaded protective clothing.

Exemplary embodiments of radiation barriers are described above in detail. The barriers are not limited to the specific embodiments described herein, but rather, components of each barrier may be utilized independently and separately from other components described herein. Each radiation barrier component can also be used in combination with other radiation barrier components.

When introducing elements of the present invention or the preferred embodiment(s) thereof, the articles "a", "an", "the" and "said" are intended to mean that there are one or more of the elements. The term "plurality" is intended to mean there are two or more of the corresponding elements. The term "multiplicity" is intended to mean that there are three or more of the corresponding elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A radiation barrier for shielding a person from radiation emitted from a radiation source, said barrier comprising:
   a radiopaque wall having opposite lateral edges, said wall being positionable between the radiation source and the person to prevent radiation from traveling directly from the radiation source to the person; and
   a radiopaque deflector adjacent an upper edge of the wall obliquely angled with respect to the wall, and extending generally toward the radiation source when the wall is positioned between the source and the person.

2. A barrier in accordance with claim 1 wherein the deflector extends from at least one lateral edge of the wall.

3. A barrier in accordance with claim 1 wherein the wall extends vertically between an upper edge and a lower edge, and said deflector extends from the upper edge.

4. A barrier in accordance with claim 1 wherein the wall extends vertically between the upper edge and a lower edge, and further comprises a lower deflector extending from the lower edge.

5. A barrier in accordance with claim 1 wherein at least a portion of the wall is transparent to visible light.

6. A barrier in accordance with claim 1 wherein at least one deflector of the side deflectors and the upper deflector is pivotally attached to the wall.

7. A barrier in accordance with claim 1 wherein at least one deflector of the side deflectors and the upper deflector has a plurality of surfaces, and each surface of the plurality of surfaces is obliquely angled with respect to another surface of the plurality of surfaces.

8. A barrier in accordance with claim 1 wherein the wall has an opening for accommodating a portion of the radiation source.

9. A barrier in accordance with claim 8 further comprising a radiopaque cover positioned over the opening for preventing radiation emitted from the radiation source from passing through the opening to the person.

10. A barrier in accordance with claim 9 wherein the cover is rotatably attached to the wall adjacent the opening, said cover having a closed position in which at least a portion of the cover is generally parallel to the wall to block radiation emitted from the radiation source from passing through at least a portion of the opening and an open position in which the cover is angled with respect to the wall to allow a portion of the radiation source to be accommodated by the opening, said rotating cover moving from the closed position to the open position when engaged by the radiation source.

11. A barrier in accordance with claim 10 wherein the cover is biased toward the closed position.

12. A barrier in accordance with claim 9 further comprising a flexible radiopaque seal attaching the cover to the wall to prevent radiation emitted from the source from passing between the cover and the wall.

13. A barrier in accordance with claim 12 wherein the flexible radiopaque seal comprises an accordion structure.

14. A barrier in accordance with claim 1 wherein the wall has an opening for accommodating a portion of a table and a portion of patient supported by the table.

15. A barrier in accordance with claim 14 further comprising a radiopaque skirt for blocking a space formed between the wall and at least one of the patient and the table to prevent radiation emitted from the source from traveling through the opening.

16. A barrier in accordance with claim 15 wherein the radiopaque skirt comprises an accordion structure.

17. A barrier in accordance with claim 14 wherein the wall comprises a lower section and an upper section detachable from the lower section, said lower section being positionable between the table and a floor supporting the table, and said upper section having the opening for accommodating a portion of the table and a portion of the patient supported by the table.

18. A barrier in accordance with claim 17 wherein a lower surface of the upper section and an upper surface of the lower section are adapted to interdigitate.

19. A barrier in accordance with claim 18 wherein the lower surface of the upper section comprises a protrusion and the upper surface of the lower section includes a recess for receiving the protrusion of the lower surface of the upper section.

20. A barrier in accordance with claim 17 wherein the lower section is supported by at least one caster to facilitate movement of the lower section.

21. A barrier in accordance with claim 17 wherein at least a portion of the upper section is transparent to visible light.

22. A barrier in accordance with claim 17 wherein said opening is a first opening and the upper section has a second opening for accommodating a portion of the radiation source.

23. A barrier in accordance with claim 17 wherein said opening is a first opening and the lower section has a second opening for accommodating a portion of the radiation source.

24. A barrier in accordance with claim 23 further comprising a flexible radiopaque panel positioned over the second opening for preventing radiation emitted from the radiation source from passing through the second opening to the person.

25. A barrier in accordance with claim 24 wherein the flexible radiopaque panel comprises an accordion structure.

26. A barrier in accordance with claim 17 further comprising a support for supporting the upper and lower sections, said support comprising a base and a moveable arm attaching the upper section of the wall to the base for supporting the upper section of the wall when detached from the lower section.

27. A barrier in accordance with claim 26 wherein the support is supported by at least one caster to facilitate movement of the wall.

28. A barrier in accordance with claim 26 wherein a portion of the lower section is movable relative to the support to allow unobstructed access to the radiation source and a portion of the patient adjacent the radiation source when the wall is positioned between the source and the person.

29. A barrier in accordance with claim 1 in combination with the radiation source.

30. A wall for shielding a person from radiation emitted from a radiation source, said wall comprising:
a support including a base and a moveable arm extending from the base;
a radiopaque lower section; and
a radiopaque upper section, having a radiopaque deflector adjacent an upper edge of the wall, mountable on the lower section and attached to the arm of the support for supporting the upper section when removed from the lower section and for selectively moving the upper section into position for mounting on the lower section, said upper section having an opening sized and shaped for accommodating a portion of a table for supporting a patient and a portion of the patient supported by the table, said upper section and said lower section being positionable between the radiation source and the person to prevent radiation from traveling directly from the radiation source to the person.

31. A wall in accordance with claim 30 wherein the support is supported by at least one caster to facilitate movement of the wall.

32. A wall in accordance with claim 30 wherein a portion of the lower section is movable relative to the support to allow unobstructed access to the radiation source and a portion of the patient adjacent the radiation source when the wall is positioned between the source and the person.

33. A wall in accordance with claim 30 further comprising a radiopaque deflector extending from at least one of the upper section and the lower section, said deflector being obliquely angled with respect at least one of the upper and lower sections.

34. A wall in accordance with claim 30 wherein said opening is a first opening and the upper section has a second opening for accommodating a portion of the radiation source.

35. A wall in accordance with claim 34 further comprising a radiopaque cover positioned over the second opening for preventing radiation emitted from the radiation source from passing through the second opening to the person.

36. A wall in accordance with claim 35 wherein the first opening is positioned in the cover.

37. A wall in accordance with claim 35 wherein the cover is rotatably attached to the upper section adjacent the second opening, said cover having a closed position in which at least a portion of the cover is generally parallel to the upper section to block radiation emitted from the radiation source from passing through at least a portion of the second opening and an open position in which the cover is angled with respect to the upper section to allow a portion of the radiation source to be accommodated by the second opening, said rotating cover moving from the closed position to the open position when engaged by the radiation source.

38. A wall in accordance with claim 37 wherein the cover is biased toward the closed position.

39. A wall in accordance with claim 35 further comprising a flexible radiopaque seal attaching the cover to the upper section to prevent radiation emitted from the source from traveling between the cover and the upper section.

40. A wall in accordance with claim 39 wherein the flexible radiopaque seal comprises an accordion structure.

41. A wall in accordance with claim 30 further comprising a radiopaque skirt for blocking a space formed between the wall and at least one of the patient and the table to prevent radiation emitted from the source from traveling through the opening.

42. A wall in accordance with claim 41 wherein the radiopaque skirt comprises an accordion structure.

43. A wall in accordance with claim 30 wherein a lower surface of the upper section is sized and shaped to receive and engage an upper surface of the lower section.

44. A wall in accordance with claim 43 wherein the lower surface of the upper section comprises a protrusion and the upper surface of the lower section includes a recess for receiving the protrusion of the lower surface of the upper section.

45. A wall in accordance with claim 30 wherein the lower section is supported by at least one caster to facilitate movement of the lower section.

46. A wall in accordance with claim 30 wherein at least a portion of the upper section is transparent to visible light.

47. A wall in accordance with claim 30 wherein said opening is a first opening and the lower section has a second opening for accommodating a portion of the radiation source.

48. A wall in accordance with claim 47 a flexible radiopaque panel positioned over the second opening for preventing radiation emitted from the radiation source from passing through the second opening to the person.

49. A wall in accordance with claim 48 wherein the flexible radiopaque panel comprises an accordion structure.

50. A wall in accordance with claim 30 in combination with the radiation source.

51. A barrier for shielding a person from radiation emitted from a radiation source, said barrier comprising:
a radiopaque central portion positionable between the radiation source and the person to prevent radiation from traveling directly between the radiation source and the person; and
a radiopaque margin at least partially surrounding the central portion along at least two adjacent edges thereof and obliquely angled with respect to the central portion.

52. A barrier in accordance with claim 51 wherein the central portion is generally planar.

53. A barrier in accordance with 51 wherein at least a portion of the margin is generally planar.

54. A radiation barrier for shielding a person from radiation emitted from a radiation source, said barrier comprising a radiopaque wall positionable between the radiation source and the person to prevent radiation form traveling directly between the radiation source and the person, said wall having an opening positioned for accommodating a portion of the radiation source and a substantially continuous and uninterrupted radiopaque cover movably attached to the wall and positioned over the opening for preventing radiation emitted from the radiation source from passing through the opening to the person.

55. A barrier in accordance with claim 54 wherein the cover is rotatably attached to the wall adjacent the opening, said cover having a closed position in which at least a portion of the cover is generally parallel to the wall to block radiation emitted from the radiation source from passing through at least a portion of the opening and an open position in which the cover is angled with respect to the wall to allow a portion of the radiation source to be accommodated by the opening, said rotating cover moving from the closed position to the open position when engaged by the radiation source.

56. A barrier in accordance with claim 55 wherein the cover is biased toward the closed position.

57. A barrier in accordance with claim 54 further comprising a flexible radiopaque seal attaching the cover to the wall to prevent radiation emitted from the source from traveling between the cover and the wall.

58. A barrier in accordance with claim 57 wherein the flexible radiopaque seal comprises an accordion structure.

59. A radiation barrier for shielding a person from radiation emitted from a radiation source, said barrier comprising:
a radiopaque wall extending between opposite lateral edges and vertically between an upper edge and a lower edge, said wall positionable between the radiation source and the person to prevent radiation from traveling directly between the radiation source and the person; and
a radiopaque deflector pivotally attached along the upper edge of the wall.

60. A barrier in accordance with claim 59 wherein the deflector is a first deflector and the barrier further comprises a second deflector extending from at least one of said lateral edges of the wall.

61. A barrier in accordance with claim 59 wherein said deflector is a first deflector and the barrier further comprises a second deflector extending from the lower edge.

62. A barrier in accordance with claim 59 wherein the deflector has a plurality of surfaces, and each surface of the plurality of surfaces is obliquely angled with respect to another surface of the plurality of surfaces.

63. A radiation barrier for shielding a person from radiation emitted from a radiation source, said barrier comprising:
a radiopaque wall positionable between the radiation source and the person to prevent radiation from traveling directly between the radiation source and the person, said wall having opposite side edges, an upper edge and a lower edge; and
a plurality of radiopaque deflectors obliquely angled with respect to at least a portion of the wall, wherein at least two of said plurality of deflectors extend from adjacent edges of the wall.

64. A barrier in accordance with claim 63 wherein the plurality of deflectors extend generally away from the radiation source when the wall is positioned between the source and the person.

65. A barrier in accordance with claim 63 wherein the plurality of deflectors extend generally toward the radiation source when the wall is positioned between the source and the person.

66. A barrier in accordance with claim 63 wherein at least one of the plurality of deflectors is pivotally attached to the wall.

67. A barrier in accordance with claim 63 wherein at least one of the plurality of deflectors has a plurality of surfaces, and each surface of the plurality of surfaces is obliquely angled with respect to another surface of the plurality of surfaces.

* * * * *